United States Patent [19]

Godwin

[11] Patent Number: 4,722,811
[45] Date of Patent: Feb. 2, 1988

[54] PROCESS FOR PREPARING GLYCOL MONOESTERS

[75] Inventor: Allen D. Godwin, Waterloo, Belgium

[73] Assignee: Exxon Research & Engineering Co., Florham Park, N.J.

[21] Appl. No.: 888,580

[22] Filed: Jul. 21, 1986

Related U.S. Application Data

[63] Continuation of Ser. No. 792,139, Oct. 28, 1985, abandoned, which is a continuation-in-part of Ser. No. 660,728, Oct. 15, 1984, abandoned.

[51] Int. Cl.$^4$ .............................................. C07C 67/26
[52] U.S. Cl. ..................... 260/410.6; 560/1; 560/101; 560/105; 560/122; 560/193; 560/200; 560/240
[58] Field of Search .................. 560/240, 105, 200, 1; 260/410.6

[56] References Cited

U.S. PATENT DOCUMENTS

| | | | |
|---|---|---|---|
| 2,335,813 | 11/1943 | Stein | 560/240 |
| 2,716,137 | 8/1955 | Patton | 560/240 |
| 2,910,490 | 10/1959 | Malkemus | 560/240 |
| 2,929,835 | 3/1960 | Hayes | 560/209 |
| 3,340,295 | 9/1967 | Wheeler | 560/240 |
| 4,069,242 | 1/1978 | Gurgiolo | 560/240 |
| 4,252,935 | 2/1981 | Anderson | 560/240 |

FOREIGN PATENT DOCUMENTS

| | | | |
|---|---|---|---|
| 1226579 | 10/1962 | Fed. Rep. of Germany | 560/240 |
| 45-31924 | 10/1970 | Japan | 560/240 |
| 660900 | 11/1951 | United Kingdom | 560/240 |
| 1119897 | 7/1968 | United Kingdom . | |

*Primary Examiner*—Michael L. Shippen
*Attorney, Agent, or Firm*—J. B. Murray, Jr.; J. J. Mahon

[57] ABSTRACT

An improved process for preparing glycol monoesters is provided which comprises reacting an alkylene oxide with a substantially hindered carboxylic acid in the presence of a hydroxy alkyl amine catalyst.

10 Claims, No Drawings

PROCESS FOR PREPARING GLYCOL MONOESTERS

CROSS-REFERENCE TO RELATED APPLICATIONS

This is a continuation of application Ser. No. 792,139, filed 10/28/85, now abandoned which is a continuation-in-part of co-pending application Ser. No. 660,728, filed 10/15/84, now abandoned.

BACKGROUND OF THE INVENTION

1. Field of the Invention

This invention relates generally to the preparation of esters of carboxylic acids and more particulary to a process for preparing glycol monoesters of sterically hindered carboxylic acids in very high selectivity.

2. Description of the Prior Art

British Pat. No. 1,119,897 relates to a process for reaction of an alkylene oxide with a sterically hindered carboxylic acid, which acid selectively favors the formation of the glycol monoester while inhibiting the formation of undesirable by-products. Catalyst disclosed for this purpose are alkali metal hydroxides, alkaline earth metal hydroxides, salts of strong basis, sodium metal, sodium alkoxides (such as sodium methylates) and, under certain conditions, mineral acids, such as sulfuric acid. Sodium hydroxide is said to be preferred.

While this method permits the efficient production of such glycol monoesters, it has not been possible heretofore to form the glycol monoesters in carboxylic acid conversions greater than about 90% without the formation of undesirably large amounts of by-product such as the di(carboxylic acid) ester of the glycol. For example, in the first example of British Pat. No. 1,119,897, the monoester was produced in high yield (81.7%), except that 7% of the unreacted neodecanoic acid and 11.1% diester and 2-mole ethoxylate impurities were present. Also, in the second example as the neo acid conversion approaches 100%, the concentration of the monoester rapidly decrease from 94.5% to 35%, with substantial increases in both diester and the 2-mole ethoxylated products effected.

Continued addition of ethylene oxide yielded higher ethoxylated products. The same effect, the very sudden and rapid decrease in a monoester concentration, as the conversion of the neo acid approach to 100%, is also noted in Example 3. These examples illustrate the difficulties in obtaining a high purity monoester product using the prior art process. The exact amount of ethylene oxide added to the reaction is required by the prior art patent to be carefully monitored in order to obtain monoester in high yield. Also, terminating the reaction before complete neo acid conversion is achieved is required in order to obtain monoester in an acceptable yield. This results in costly separation schemes in order to remove the unreacted neo acid from the desired monoester product.

In addition, the use of potassium or sodium hydroxides as catalyst has the disadvantage of forming water of reaction arising as a result of the neutralization of the neo acid reactant and the alkali metal hydroxide catalyst. Since water is an undesired contaminant, which can lead to by-product formations, the control of this water content is a process disadvantage.

SUMMARY OF THE INVENTION

An improved process for preparing glycol monoesters is provided which comprises reacting an alkylene oxide with a sterically hindered carboxylic acid in the presence of catalyst comprising hydroxy alkyl amines.

It has been surprisingly found that the use of the hydroxy alkyl amine catalyst of this invention permits the selected glycol monoester to be formed in very high selectivities at high conversions of the sterically hindered acid which is charged, thereby minimizing or substantially avoiding the formation of the undesirable by-products such as the glycol diesters. Unlike prior art processes, it is not necessary when using the method of this invention to avoid the absence of excess alkylene oxide or to terminate the esterification reaction prior to complete conversion of the carboxylic acid charged. It has been surprisingly found by use of the process of this invention that the di-ester by-products are not rapidly formed after consumption of the sterically hindered carboxylic acid. Therefore, the need to perform the extensive and time-consuming periodic analyses of the reaction mixture to determine the end-point of glycol monoester specificity is not necessary as is the case in use of prior art methods.

DETAILED DESCRIPTION OF THE INVENTION

In accordance with this invention, a process is provided whereby, in the presence of an anhydrous hydroxy alkyl amine catalyst, an alkylene oxide is reacted with a sterically hindered carboxylic acid, to form the glycol monoester in high selectivity and at high conversions of the acid charged, while minimizing the formation of undesirable by-products. Thus, the present invention provides a practical method for upgrading the production of glycol monoesters while utilizing readily available materials.

The sterically hindered carboxylic acid is defined as a carboxylic acid having a tertiary carbon atom in the alpha, beta, or gamma position with respect to the carboxylic group.

Acids applicable to the present process include any neo carboxylic acid, a neo carboxylic acid being defined herein as a carboxylic acid wherein the carboxyl group is attached to a tertiary carbon atom. By tertiary carbon atom is meant a carbon atom which does not have attached to it a hydrogen atom. In these neo acids the carbon atom attached to the carboxyl group viz., the "alpha carbon", will be connected to three organic radicals, each through a carbon atom. While monocarboxylic acids are most common, the process of this invention will be equally applicable to reactions involving di- and poly-carboxylic acids. (In short, therefore, the acids employed in this invention include alkanoic acids having a tertiary alpha carbon atom attached to each carboxylic acid group.) The term "alkanoic acid" is intended to include cyclic and acyclic compounds, either mono-, di-, or polycarboxy compounds, as previously noted.

To clarify further the definition of a neo carboxylic acid, reference may be had to the following structure.

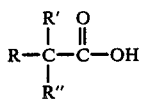

wherein each R is an organic radical.

In the most common case, R, R', and R" will represent an aryl, alkyl, aralkyl, or alkaryl radical of from 1 to 20 carbon atoms. The di- and poly-carboxylic acids of this process will have one or more of the carboxyl groups attached to a tertiary carbon atom, e.g.,

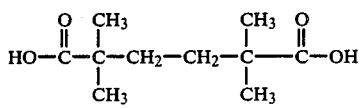

where each carboxyl group in a polycarboxylic compound is attached to a tertiary carbon atom, the compound will be fully sterically hindered. On the other hand, there are many di- and polycarboxylic acid compounds available wherein only one or, in any event, less than all, of the carboxylic groups attached to a tertiary carbon atom. In this latter case, the unhindered carboxylic group will react with an alkylene oxide in a known manner and form a random product distribution of monoesters, diesters, and higher esters. However, the sterically hindered carboxyl group will react in accordance with the present invention to yield glycol monoesters with high selectivity and yields.

In addition to the neo acid structure, other sterically hindered acids are applicable to this process. As a general rule, normal or straight chain alkanoic acids are considered to be unhindered and will react to form the random product distribution described above, whereas branching tends to create various degrees of steric hindrance. While neo acids are sterically hindered, branching on the beta and gamma carbon atoms similar to that described above for the alpha carbon atom also results in sterically hindered acids, e.g.,

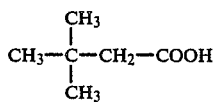

Steric hindrance is described on pages 204–217 of "Steric Effects on Organic Chemistry", edited by Melvin Newman (1956). As evidenced by this text, the branched acids, and especially those having tertiary alpha, beta or gamma carbon atoms, usually have an extremely low rate of esterification, indicating substantial steric hindrance.

Having broadly defined the carboxylic acids which may be reacted in accordance with the present process, specific examples of these hindered mono-, di-, and polycarboxylic acids are listed below for purposes of illustration, it being understood that the specific list is for illustrative purposes only and not intended to define the scope of this invention. Homologues and analogues of the specific compounds listed and having a branched or tertiary alpha, beta, or gamma carbon atom are within the framework of this invention.

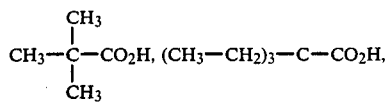

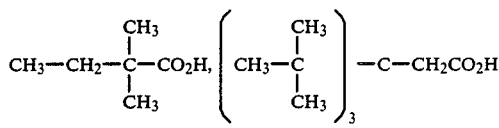

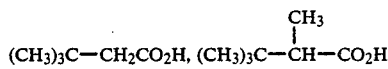

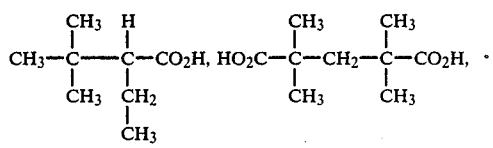

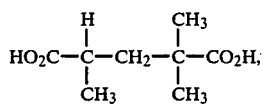

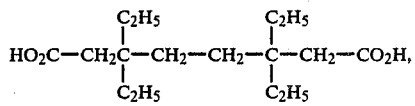

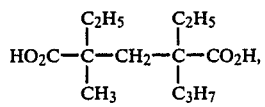

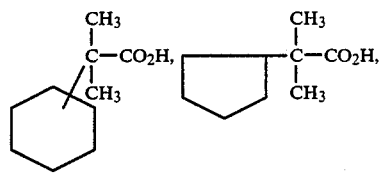

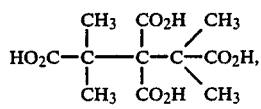

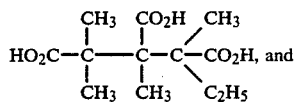

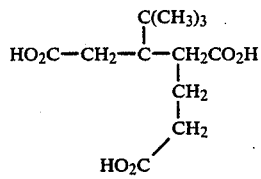

Halogen may be substituted for an alpha or beta hydrogen or R group in any of the above examples.

Preferred neo acids comprise compounds of structure (I) wherein R' and R" are each $C_1$-$C_3$ hydrocarbyl radicals, and R is $C_1$ to $C_6$ alkyl. Some typical examples of neo acids are: trimethylacetic acid; alpha, alpha-dimethyl cyclohexylacetic acid; alpha, alpha-dimethyl heptanoic acid; and the like. These neo acids can also be prepared by the well known Koch process from carbon monoxide, water and type II, III, IV or V olefins as described by H. Koch in BrenntstaffChem. 36, 321 (1955). Further details on methods for making neo-acids can be found in British Pat. No. 998,974 and U.S. Pat. No. 3,349,107 all of which are incorporated herein by reference. Neo acids are often made from branched chain olefin feedstocks which are random isomeric mixtures in regard to the position of the olefinic bond. These acids are thus random isomeric mixtures of neo acids. These neo acids are suitable in their isomeric forms, or any suitable mixtures thereof may be employed for the reaction to form the corresponding monoester mixtures.

The neo acids may be prepared directly from olefins, carbon monoxide, and water in a one step process. An alternative to the one step process is a two step process, whereby in the first step an olefin and carbon monoxide are reacted in the presence of an acidic catalyst, essentially in the absence of water, to form an intermediate hydrolyzable reaction product which is then hydrolyzed in the second step to liberate the desired carboxylic acid product.

The sterically hindered carboxylic acids when added to the reaction mixture should preferably be free of water, e.g., the acids should contain <0.1 wt. % water.

Alkylene oxides which may be used in the present invention are the 1, 2-oxides. A preferred group within this class are the lower alkylene oxides having from 2 carbon atoms to 8 carbon atoms in the hydrocarbon chain, ethylene oxide being particularly preferred. Other representative alkylene oxides are propylene-1,2 oxide, butylene-1,2 oxide, styrene oxide, epichlorohydrin, and glycidyl ethers. It is preferred that water be kept out of the alkylene oxide since its presence will lead to the undesirable formation of polyalkylene glycol, which in turn will inhibit the process of this invention.

Water in the reaction mixture should be substantially avoided, and preferably the water content will be less than about 0.05 mol. %.

The catalysts as added to the reaction mixture in the practice of this invention must be anhydrous and comprise at least one hydroxy alkyl amine of the formula (I):

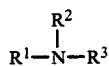
(I)

wherein $R^1$, $R^2$ and $R^3$ are the same or different and are H or hydroxy-substituted alkyl, with the proviso that at least one of $R^1$, $R^2$ and $R^3$ is hydroxy-substituted alkyl. Therefore, suitable catalysts of this invention comprise mono (hydroxy alkyl) amines of the formula (II):

$$R^1-NH_2 \quad (II)$$

wherein $R^1$ is hydroxy-substituted alkyl; di(hydroxy alkyl) amines of the formula (III):

(III)

wherein $R^1$ and $R^2$ are the same or different and are each hydroxy-substituted akyl; and tri(hydroxy alkyl) amines of the formula (IV):

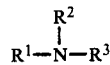
(IV)

wherein $R^1$, $R^2$ and $R^3$ are the same or different and are each hydroxy-substituted alkyl.

Examples of $R^1$, $R^2$ and $R^3$ substituents of the hydroxy alkyl amines of each of the above formulas are hydroxy-substituted alkyl radicals derived from straight and branched-chained alkanes of from about 1 to 20 carbon atoms, preferably from about 1 to 12 carbon atoms, and most preferably from about 2 to 4 carbon atoms (such as methyl, ethyl, isopropyl, butyl decyl, dodecyl, isostearyl, and the like). The hydroxy alkyl groups can be substituted by one or more hydroxy groups, and the OH-groups can be substituted for any carbon atom of the alkyl moiety. Preferably, each hydroxy alkyl group is mono-OH-substituted and the OH-substitution is to a carbon atom which is at least one carbon atom removed from the N atom. Exemplary primary amines are methanolamine, amine, propanol amine, ethanolamine, butanol amine, isobutanol amine, $H_2NCH(OH)CH_3$ and the like. Exemplary secondary amines are diethanolamine, butylethanol amine, dimethanol amine, dibutanol amine, and the like. Illustrative tertiary amines are:
tri-n-propanol amine,
tri-ethanol amine,
$(CH_3OH)_2N(CH_2CH_2OH)$,
$(OHCH_2CH_2)N(CH_2CH(OH)CH_3)$,
$(HOCH_2)_2N(CH_2CH_2CH_2OH)$,

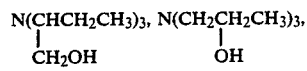

and the like.

Preferred hydroxy alkyl amine catalysts of this invention are diethanol amine and triethanol amine.

The hydroxy alkyl amine catalysts of this invention will be generally charged to the reaction mixture in an amount of from about 0.1 to 5 mol. %, and preferably from about 0.5 to 2 mol. %, based on the sterically hindered neo acid charged.

The advantage of this invention lies in the ability to produce very high yields of substantially pure glycol monoesters at up to 100% neo acid conversions, thus eliminating the necessity for costly separation procedures.

According to the present invention an alkylene oxide is reacted with a sterically hindered carboxylic acid at an elevated temperature. The optimum conditions suitable for accomplishing glycolmonoester formation depend on the type of sterically hindered carboxylic acid used in the reaction mixture. A temperature range of from about 80° to 200° C. will be generally used, with temperatures of from about 140° to 185° C. being preferred, and with temperatures of from about 140° to 165° C. being especially preferred. Temperatures above 200° C. are operable; however, in practice such temperatures tend to decrease the proportion of glycol monoester in the product. Pressure is not critical but the reaction should be carried out in the range of from atmospheric pressure to about 100 psig, with a range of from atmospheric pressure to about 80 psig being preferred.

The alkylene oxide is added to the sterically hindered carboxylic acid until the reaction is complete. It is known that glycol monoester formation depends on the presence of unreacted acid. However, the use of the sterically hindered acid promotes a high degree of selectivity to the glycol monoester while inhibiting formation of higher esters which would ordinarily form if a sterically hindered acid were not used. Unreacted acid is not essential for the selective formation of the glycol monoester using the process of this invention, unlike prior art processes. Therefore, the alkylene oxide can be employed, if desired, in an excess over that stoichiometrically required to react with the sterically hindered acid. Therefore, the need for frequent and periodic analyses of the reaction mixture to establish the end point of the reaction is avoided.

It is known that reactions between alkylene oxides and carboxylic acids result in a random distribution of alkylene oxide in the products when the alkylene oxide is added in excess. The same is true in this process; however, it was discovered that by employing my amine catalysts in combination with sterically hindered carboxylic acids, glycol monoester was the initial reaction product, and the rapid formation of polyalkylene oxide esters and glycol dicarboxylic acid esters which occurred in prior art processes after the consumption of the carboxylic acid, are avoided. Thus, the periodic analysis were not acquired. The reaction is preferably terminated when 1.03 to 1.05 molar equivalent of alkylene oxide is added.

Another advantage of this process is that undesirable inorganic salts are not present in the monoester product.

Distillation can be performed to recover the monoester reaction product formed by the method of this invention, if desired. This method of recovery is only illustrative and is not meant to limit in any way the subject of this invention. If desired, the monoester thereby obtained can also be further purified by such standard methods as: stripping at about 160° C. under vacuum, treatment with activated alumina, attapulgus clay or celite (with or without the presence of charcoal), molecular distillation and the like. Therefore, water washing, as used in the prior art, is not required, and the reaction product mixture containing the desired monoester product can be used directly, as for example, as feed to a second reaction zone in which the monoester is contacted with a mono- or poly-basic carboxylic acid (such as aromatic acids, e.g., benzoic, toluic, phthalic, terephthalic, and dimethylbenzoic acids; dibasic aliphatic carboxylic acids, e.g., adipic, subasic, maleic, and subaric acids; and the like) to form a diester which can be used as a plasticizer or lubricant. A preferred such reaction is described in co-pending application Ser. No. 661,425, filed Oct. 15, 1984, the disclosure of which is hereby incorporated by reference.

The improved process and compositions of this invention can be further illustrated by reference to the following examples:

EXAMPLES 1-2

Preparation of Ethylene Glycol Mono-neononanoate

To a one liter stainless steel autoclave, equipped with a mechanical stirrer, heater, cooling coils, automatic temperature controller, and a tared ethylene oxide cylinder, in a series of runs is added 500 grams neononanoic acid and 2.0 g of the selected catalyst. The reactor is heated to approximately 100° C. and a gaseous $N_2$ purge of the reactor is introduced to remove both oxygen and water. With continued $N_2$ purging its temperature of the neo acid/catalyst solution is gradually raised to 150° C. Upon reaching temperature, the $N_2$ purge is stopped and the reactor vents are sealed. Ethylene oxide is then slowly added to the reactor until a pressure of 60 psig is obtained. The ethylene oxide flow is then stopped. As the reaction between the neo acid and the ethylene proceeds, the pressure of the reactor vessel will slowly decrease. When the pressure reaches 20 psig, ethylene oxide is again slowly charged to the reactor until a pressure of 60 psig is obtained. The ethylene oxide flow is then decreased to the point where a steady reactor pressure of 60 psig is obtained. The addition of ethylene oxide continues until the desired quantity of ethylene oxide has been added to the reaction. The flow of ethylene oxide is then stopped. The reaction mixture is stirred for an additional 20 minutes, until the reactor pressure decreases to 15 psig. Total reaction time, from the start of ethylene oxide addition is about 55 minutes. The reactor is then vented, a gaseous nitrogen purge is introduced, and the reaction product is cooled to room temperature. The crude ethylene glycol mononeononanoate product mixture thereby obtained was characterized by gas chromatography and found to have the following characteristics:

| | |
|---|---|
| Color, Pt/Co Scale | 30 |
| Specific gravity 20/20 | 1.0362 |
| Refractive index | 1.490 |

The results thereby obtained are set forth in Table I below:

| | |
|---|---|
| Examples 1 and 2 catalyst = | diethanolamine $(HN[CH_2CH_2OH]_2)$ |
| Comparative Examples 1 = A, B and C catalyst | potassium hydroxide |
| D catalyst = | dimethyl formamide |

TABLE I

| | | Ethylene Oxide Charged | | Product Mixture Analysis (GC) (wt %) | | | |
|---|---|---|---|---|---|---|---|
| Example No. | Catalyst Charged | (grams) | (Mole/Mole Neo-Acid) | Neo-Acid (1) | Mono-Ester (2) | Diethoxylate | Diester |
| 1 | DEA | 160 | 1.25 | — | 9.79 | 2.1 | — |
| 2 | DEA | 180 | 1.41 | — | 97.8 | 2.1 | <0.1 |
| Comparative Ex. A | KOH | 160 | 1.25 | — | 54.9 | 14.6 | 30.5 |
| Comparative Ex. B | KOH | 164 | 1.28 | — | 51.1 | 15.5 | 33.4 |
| Comparative Ex. C | KOH | 160 | 1.25 | — | 55.3 | 10.2 | 34.5 |
| Comparative | DMF | 172 | 1.34 | — | 95.3 | 2.9 | 1.8 |

TABLE I-continued

| Example No. | Catalyst Charged | Ethylene Oxide Charged (grams) | Ethylene Oxide Charged (Mole/Mole Neo-Acid) | Product Mixture Analysis (GC) (wt %) Neo-Acid (1) | Product Mixture Analysis (GC) (wt %) Mono-Ester (2) | Product Mixture Analysis (GC) (wt %) Diethoxylate | Product Mixture Analysis (GC) (wt %) Diester |
|---|---|---|---|---|---|---|---|
| Ex. D | | | | | | | |

Notes:
DEA = diethanolamine; DMF = diemethylformamide; KOH = potassium hydroxide.
(1) neo-acid = neo-decanoic acid.
(2) mono-ester = ethylene glycol mono-neodecanoate.

EXAMPLES 3 AND 4

Preparation of Ethylene Glycol Mono-neodecanoate

To a one liter stainless steel autoclave, equipped with a mechanical stirrer, heater, cooling coils, automatic temperature controller, and a tared ethylene oxide cylinder, in a series of runs is added 500 grams neodecanoic acid and 2.0 g of the selected catalyst. The reactor is heated to approximately 100° C. and a gaseous N₂ purge of the reactor is introduced to remove both oxygen and water. With continued N₂ purging its temperature of the neo acid/catalyst solution is gradually raised to 150° C. Upon reaching temperature, the N₂ purge is stopped and the reactor vents are sealed. Ethylene oxide is then slowly added to the reactor to maintain a reactor pressure of about 30 psig. The flow of ethylene oxide is then stopped. The reaction mixture is stirred for an additional 20 minutes, until the reactor pressure decreases to 15 psig. Total reaction time, from the start of ethylene oxide addition is about 55 minutes. The reactor is then vented, a gaseous nitrogen purge is introduced, and the reaction product is cooled to room temperature. The crude ethylene glycol mononeodecanoate product mixture thereby obtained was analyzed by gas chromatography. The data obtained are set forth in Table II below.

TABLE II

| Example No. | Catalyst Charged | Ethylene Oxide Charged (grams) | Ethylene Oxide Charged (Mole/Mole Neo-Acid) | Neo-Acid (1) | Mono-Ester (2) | Diethoxylate | Diester |
|---|---|---|---|---|---|---|---|
| 3 | TEA | 136 | 1.06 | — | 96.4 | 2.68 | 0.88 |
| 4 | TEA | 137 | 1.07 | — | 96.8 | 2.53 | 0.63 |
| Comparative Ex. E | TOA | 138 | 1.08 | — | 96.2 | 3.08 | 0.68 |
| Comparative Ex. F | TOA | 137 | 1.07 | — | 92.0 | 3.65 | 4.37 |
| Comparative Ex. G | TOA | 135 | 1.09 | — | 93.6 | 3.6 | 2.41 |
| Comparative Ex. H | TOA | 139 | 1.05 | — | 93.8 | 3.58 | 2.64 |
| Comparative Ex. I | DMOA | 138 | 1.08 | — | 84.3 | 5.20 | 10.5 |
| Comparative Ex. J | DMOA | 138 | 1.08 | — | 83.2 | 5.61 | 11.2 |

Notes:
TEA = triethanolamine; TOA = tri-n-octylamine; DMOA = dimethyl n-octylamine.
(1) neo-acid = neo-decanoic acid.
(2) mono-ester = ethylene glycol mono-neodecanoate.

From the foregoing description, one skilled in the art can easily ascertain the essential characteristics of this invention and without departing from the spirit and scope thereof can make various changes and/or modifications to the invention for adapting it to various usages and conditions. Accordingly, such changes and modifications are properly intended to be within the full range of equivalents of the following claims.

What is claimed is:

1. In a method for preparing glycol monoesters by reacting an alkylene oxide with a sterically hindered neo carboxylic acid of the formula:

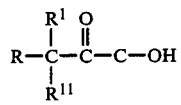

where R, $R^1$ and $R^{11}$ represent aryl, alkyl, aralakyl or alkaryl radicals having 1 to 20 carbon atoms in the presence of a catalyst, the improvement which comprises employing a catalyst for the reaction consisting of at least one hydroxy alkyl amine.

2. The improved method according to claim 1 wherein the alkylene oxide comprises a 1,2-alkylene oxide.

3. The improved method of claim 2 wherein the alkylene oxide is ethylene oxide or propylene oxide.

4. The improved method of claims 1, or 2 wherein the hydroxy alkyl amine catalyst comprises at least one member selected from the group consisting of compounds of the formula:

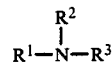

wherein $R^1$, $R^2$ and $R^3$ are the same or different and are each H or hydroxy alkyl, with the proviso that at least one of $R^1$, $R^2$ and $R^3$ comprise hydroxy alkyl.

5. The improved method of claims 1, or 2 wherein said hydroxy alkyl amine catalyst comprises at least one compound of the formula:

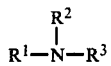

wherein $R^1$, $R^2$ and $R^3$ are the same or different and are each hydroxy alkyl of from about 1 to 20 carbon atoms.

6. The improved process of claims 1, or 2 wherein said hydroxy alkyl amine catalysts comprises diethanol amine or triethanol amine.

7. The improved method according to claim 6 wherein said amine catalyst is employed in an amount of from about 0.1 to 5 mol %, based on the sterically hindered carboxylic acid charged to the reaction mixture.

8. The improved method according to claim 7 wherein said reaction is effected at pressures of from atmospheric to about 100 psig.

9. The improved method according to claim 7 wherein said reaction is effected at a temperature of from about 80° to 200° C.

10. The process of claim 1 wherein $R^1$ and $R^{11}$ are $C_1$–$C_3$ hydrocarbyl and R is $C_1$–$C_6$ alkyl.

* * * * *